United States Patent
Kadkhodayan et al.

Patent Number: 5,235,095
Date of Patent: Aug. 10, 1993

[54] PREPARATION OF OPTICALLY ACTIVE ALIPHATIC CARBOXYLIC ACIDS

[75] Inventors: Abbas Kadkhodayan; Deepak R. Patil; Azfar A. Choudhury, all of Orangeburg, S.C.

[73] Assignee: Ethyl Corporation, Richmond, Va.

[21] Appl. No.: 825,593

[22] Filed: Jan. 24, 1992

[51] Int. Cl.$^5$ ............................................. C07B 57/00
[52] U.S. Cl. ............................................. 560/218; 548/531; 549/71; 558/414; 560/9; 560/56; 560/59; 560/61; 560/100; 560/102; 560/105; 560/125; 560/126; 560/128; 560/147; 560/248; 562/401
[58] Field of Search ........................ 562/401; 548/531; 549/71; 560/9, 56, 59, 61, 100, 102, 105, 125, 126, 128, 147, 218, 248, 265; 558/414

[56] References Cited

U.S. PATENT DOCUMENTS

| | | | |
|---|---|---|---|
| 4,694,100 | 9/1987 | Shimizu et al. | 560/105 |
| 4,723,033 | 2/1988 | Erickson | 560/56 |
| 4,752,417 | 6/1988 | Inoue et al. | 562/401 |
| 4,831,147 | 5/1989 | Russell | 562/401 X |
| 4,973,745 | 11/1990 | Blaschke et al. | 562/401 |
| 4,983,765 | 1/1991 | Lukas et al. | 562/401 |
| 5,015,764 | 5/1991 | Manimaran et al. | 562/401 |

*Primary Examiner*—Jose G. Dees
*Assistant Examiner*—Vera C. Clarke
*Attorney, Agent, or Firm*—Richard J. Hammond

[57] ABSTRACT

An improved process for the separation of enantiomers of a racemic mixture of certain aliphatic carboxylic acids or esters thereof is disclosed. The process involves: (i) forming a salt solution comprising said racemic mixture of a $C_1$ to $C_6$ linear or branched aliphatic carboxylic acid and an organic or inorganic base; (ii) treating said salt solution with one-half molar equivalent of a chiral organic nitrogenous base having a base strength no stronger than said organic or inorganic base; and (iii) precipitating from the reaction solution formed in step (ii) the less soluble diastereomeric salt, the improvement being adding to the salt solution of step (ii) an inert organic or inorganic base that is soluble in the salt solution.

16 Claims, No Drawings

PREPARATION OF OPTICALLY ACTIVE ALIPHATIC CARBOXYLIC ACIDS

FIELD OF INVENTION

This invention relates to an improvement in a process for the preparation of optically active carboxylic acids and the esters thereof. More particularly this invention relates to an improved process for the preparation of aliphatic carboxylic acids and the esters thereof by adding to a mixture of the diastereomeric salts of such materials an organic or inorganic salt.

BACKGROUND OF THE INVENTION

Resolution of racemic aryl-substituted aliphatic carboxylic acids has been described in the literature. Kaiser et al., *J. Pharm. Sci.*, Vol. 65, No. 2, 269-273 (February 1976) formed the S(−) α-methylbenzylamine salt of S(+)-ibuprofen, removed it from the reaction mixture by filtration, and recrystallized it from isopropanol and then from methanol. After acidifying the 3N aqueous sulfuric acid and extracting with ether, S(+)-ibuprofen was obtained, m.p. 50·14 52·, $[\alpha]_{D+}57\cdot$, with 95% optical purity as determined by GLC analysis. Cox et al., *J. Pharmacol. Exp. Ther.*, Vol. 232, No. 3, 636-643 (March 1985), using the Kaiser et al. method, were able to obtain an S(+)-ibuprofen preparation which was 99% S isomer and 1% R isomer (w/w).

Other methods of separating the enantiomers of racemates can be effected by preparing a salt of the acid with an alkaloid or similar resolving agent such as cinchonidine, then separating the products by fractional crystallization from a solvent in which the salt of the dextrorotatory isomer is less soluble. The (+)-salt can then be acid cleaved to yield pure enantiomer. See, for example, U.S. Pat. No. 4,209,638 issued Jun. 24, 1980, and U.S. Pat. No. 3,637,767 issued Jan. 25, 1972, which relate to resolution of naproxen and related compounds.

U.S. Pat. No. 5,015,764 discloses and claims a process for increasing the amount of the desired enantiomer obtained from a racemic mixture of $C_1$ to $C_6$ linear or branched aliphatic carboxylic acid or ester thereof. The process comprises: (i) forming a salt solution comprising the racemic mixture of the $C_1$ to $C_6$ linear or branched aliphatic carboxylic acid or ester thereof and an organic or inorganic base; (ii) treating said salt solution with a chiral organic nitrogenous base having a base strength no stronger than said organic base, inorganic base or mixtures of an organic base and an inorganic base; (iii) precipitating from the reaction solution produced in the treatment of step (ii) the less soluble diastereomeric salt; and (iv) separating said diastereomeric salt. The disclosure of this patent is incorporated herein by reference.

When reaction steps (i), (ii) and (iii) are carried out as disclosed, a two-phase mixture is produced that is essentially the solid diastereomeric salt and the remaining reaction liquid. The solid is dispersed in near emulsion form throughout the liquid. It is typically separated by filtration leaving the mother liquor filtrate and the solid filtered residue. The residue requires numerous recrystallizations before a product of satisfactory purity is obtained. Accordingly, these conventional separation processes are inconvenient and time consuming, disadvantageously producing multiple process streams.

It has now been discovered that an improved crystalline product can be obtained from the mixture of step (iii) by adding to the salt solution of step (i) an organic or inorganic salt soluble in said salt solution. In addition to the requirement for solubility in the reaction mass formed in step (i), the inorganic or organic salt must be inert to (not reactive with) the reactants. It has been discovered that from about 0.1 to about 10.0 moles of such organic or inorganic salt, based on the moles of organic or inorganic base, must be added to effectively promote the separation occurring in step (iii) of the process. Preferably about 0.5 to about 5.0 moles, most preferably an equimolar amount, based on the organic or inorganic base are added.

The soluble, inert organic or inorganic salt is preferably an alkali metal, alkaline earth metal or ammonium salt, most preferably sodium, potassium or ammonium salts of the halides (fluoro, chloro, bromo or iodo salts). Nitrates and acetate salts are also useful in the process of the present invention. Especially preferred is sodium chloride. It should be noted that, while the addition of the above soluble, inert salts to step (i) is most preferred, such salt can also be added later in the process [steps (ii) or (iii)] and will produce improved separation of the less soluble diastereomeric salt.

The $C_1$ to $C_6$ linear or branched aliphatic carboxylic acids and esters useful in the improved process of the present invention have the formula

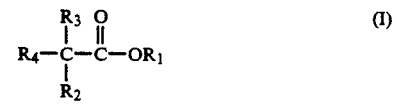

where $R_1$ is hydrogen or $C_1$ to $C_6$ linear or branched alkyl; $R_2$, $R_3$ and $R_4$ are independently different and are hydrogen or $C_1$ to $C_6$ linear or branched alkyl, e.g., methyl or ethyl; aralkyl, e.g., benzyl; cycloalkyl, e.g., cyclopropyl, cyclobutyl, cyclopentyl, cyclohexyl; alkyl substituted cycloalkyl, e.g., methylcyclohexyl; $C_6$ to $C_{10}$ aryl, e.g., phenyl unsubstituted or substituted with, for example, methyl, dimethyl, butyl, especially isobutyl or phenyl substituted with $C_1$ to $C_4$ alkylthio, $C_1$ to $C_4$ alkoxy, cyano or halo, e.g., fluoro or chloro; $C_1$ to $C_6$ linear or branched alkoxy, e.g., phenoxy or phenoxy substituted with, for example, methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkylthio; $C_6$ to $C_{10}$ arylthio; $C_6$ to $C_{10}$ arylcarbonyl, e.g., benzoyl; $C_4$ to $C_8$ cycloalkenyl, e.g., cyclohexenyl; trifluoromethyl; halo, e.g., fluoro or chloro; $C_4$ to $C_5$ heteroaryl, e.g., furyl, pyrrolyl, thienyl; or $C_{10}$ to $C_{14}$ aryl, e.g., naphthyl or naphthyl substituted with $C_1$ to $C_4$ alkyl, e.g., methyl; $C_1$ to $C_4$ alkoxy, e.g., ethoxy, halo; or biphenyl unsubstituted or substituted with methyl or halo, especially fluoro.

Preferred compounds of formula I are those of the formula

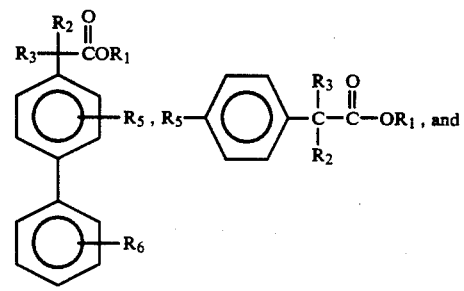

-continued

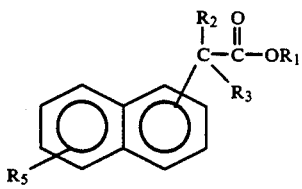

where $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The improved process is particularly applicable to 2-(4-isobutylphenyl) propionic acid and especially in obtaining a preponderance of the S(+) isomer.

The process is carried out by using a racemic mixture [a mixture of both the (+) and (−) or dextro and levo rotatory forms] or a mixture containing a preponderance of one of the enantiomers of these carboxylic acids. The use of racemic mixtures is preferred. However, it should be understood that in this step, the process itself does not convert one form of the stereoisomers to the other form but only separates such forms. Further, because the separation of isomers gives rise to a soluble product largely containing one enantiomer and an insoluble product largely containing the other enantiomer, a high purity salt is obtained that requires a minimum number of recrystallizations (usually not more than two) to give a product with exceptional high optical purity.

The purified salt obtained from the process of the present invention may be further treated to produce the free aliphatic carboxylic acid thereof by using any conventional means. For example, hydrolysis of the salt with a dilute mineral acid and extraction with a suitable organic solvent produces the purified aliphatic carboxylic acid. Further extraction and recrystallization with a suitable solvent can increase the purity to even greater extent.

The first step in the reaction sequence for the separation of the racemic mixtures used in the present invention is to form a salt solution of the aliphatic carboxylic acid with an organic or inorganic base, adding to such reaction mass the above disclosed organic or inorganic salt not reactive with but soluble in said salt solution. Where such organic base is used in this first step, the solvent employed to form the salt solution is preferably a liquid, inert, organic one. Most preferably, such solvents include the aliphatic hydrocarbon solvents, i.e., $C_4$ to $C_{14}$ hydrocarbons. Particularly preferred are hexane, octane, alcohol or water as such solvent.

The chiral organic nitrogenous base is next added. It forms a more stable salt with the isomers of the aliphatic carboxylic acid displacing the inorganic or organic base. Further, one of the diastereomeric salts formed from the subsequent displacement of the inorganic or organic base by the chiral organic nitrogenous base is more soluble in the reaction solution (the solution formed when the chiral base is added to the salt solution); the other, of course, precipitates. The solid precipitate is readily separated from the solution by conventional techniques, i.e., centrifugation, filtration and the like.

It should be noted that the process of the present invention is particularly adapted to the economical conversion of racemic mixtures to the diastereomeric S− or (+)- component. (Of course, the R-component may be the least soluble one, in which case the following discussion should be applied in reverse). The method of the present invention essentially provides a solid precipitate enriched in the S-enantiomer and a liquid filtrate enriched in the R-enantiomer. Liberation of the desired S-enantiomer from the precipitated salt is readily accomplished by acidification of the salt with, for example, dilute mineral acid or any other inorganic or organic acid conventionally known to hydrolyze salts of this nature. While this procedure leaves the filtrate as an undesired by-product, it can be further treated with acid or base to convert the R-enriched filtrate to the racemic mixture. This mixture can then be reused in the process of the present invention, using the chiral organic base recovered from the above conversion step. Thus, the process of the present invention lends itself readily to a recycling-type of procedure.

EXAMPLES

The invention is illustrated by the following Examples.

EXAMPLE 1

To a 3-liter reactor equipped with an agitator, addition funnel, thermometer and a reflux condenser were charged 200 grams (0.971 mole) of racemic ibuprofen, 21 grams of sodium chloride (0.359 mole), 63 grams of triethylamine (0.624 mole) and 570 grams of water (31.7 moles). The materials in the reactor were heated to 70° C. under vigorous agitation. 43 grams of (S)-methylbenzyl amine (0.355 mole) were fed to the reactor over two hours. Crystals of ibuprofen-(S)-methylbenzyl amine salt precipitated during the course of the reaction. The reactor contents were further agitated for two hours and were then cooled to 20°-25° C. and filtered. The solids were washed with water, dried and analyzed. The 115 grams of recovered solids represent 99% recovery based on (S)-methylbenzyl amine. The salt was acidified to liberate the optically enriched ibuprofen — 60% ee or 80% S-isomer.

EXAMPLE 2

Using the method described in Example 1, but increasing the sodium chloride content to 63 grams (1.08 moles), 115.8 grams of solids were recovered. These solids represent quantitative yield based on (S)-methylbenzyl amine. The optical purity of ibuprofen liberated from the salt was similar to that from Example 1.

EXAMPLE 3

Using the method described in Example 1, but eliminating the sodium chloride charge, only 110 grams of dry solids were recovered in 95% yield. The optical purity of ibuprofen liberated from the salt was similar to that from Example 1.

We claim:

1. In a process for separating the enantiomers of a racemic mixture of a $C_1$ to $C_5$ linear or branched aliphatic carboxylic acid or ester thereof, having the formula:

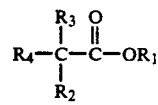

where $R_1$ is hydrogen or $C_1$ to $C_6$ linear or branched alkyl, $R_2$, $R_3$ and $R_4$ are independently different and are hydrogen or $C_1$ to $C_6$ linear or branched alkyl; aralkyl; alkyl substituted cycloalkyl; phenyl unsubstituted or substituted with methyl, dimethyl, butyl, $C_1$ to $C_4$ alkylthio, $C_1$ to $C_4$ alkoxy, cyano or halo; $C_1$ to $C_6$ linear or branched alkoxy; phenoxy or phenoxy substituted with methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio; $C_2$ to $C_8$ cycloalkylthio; $C_6$ to $C_{10}$ arylthio; $C_6$ to $C_{10}$ arylcarbonyl; $C_4$ to $C_8$ cycloalkenyl; trifluoromethyl; halo; $C_4$ to $C_5$ heteroaryl; or naphthyl or naphthyl substituted with $C_1$ to $C_4$ alkyl; $C_1$ to $C_4$ alkoxy or halo; or biphenyl unsubstituted or substituted with methyl or halo; the process comprising:

i) forming a salt solution of said racemic mixture and an organic or inorganic base;

ii) treating said salt solution with a chiral organic nitrogenous base having a base strength no stronger than said organic or inorganic base;

iii) precipitating from the reaction solution formed in step (ii) the less soluble diastereomeric salt; and iv) separating the precipitated less soluble diastereomeric salt, the improvement comprising adding to the salt solution of step (i) an organic or inorganic salt soluble in said salt solution.

2. The process according to claim 1 wherein from about 0.1 to about 10.0 moles of organic or inorganic salt is added to the salt solution based on the moles of organic or inorganic base.

3. The process according to claim 2 wherein about 0.5 to about 5.0 moles of organic or inorganic salt is added.

4. The process according to claim 3 wherein an equimolar amount of said salt is added.

5. The process according to claim 1 wherein said organic salt is an alkali metal, alkaline earth metal or ammonium acetate salt.

6. The process according to claim 5 wherein said salt is a sodium, potassium or ammonium salt.

7. The process according to claim 1 wherein said inorganic salt is an alkali metal, alkaline earth metal or ammonium salt.

8. The process according to claim 7 wherein said salt is a sodium, potassium or ammonium salt.

9. In a process for separating the enantiomers of a racemic mixture of a $C_1$ to $C_6$ linear or branched aliphatic carboxylic acid or ester thereof, the process comprising: (i) forming a salt solution of said racemic mixture and an organic or inorganic base; (ii) treating said salt solution with a chiral organic nitrogenous base having a base strength no stronger than said organic or inorganic base; and (iii) precipitating from the reaction solution formed in step (ii) the less soluble diastereomeric salt; and (iv) separating the precipitated less soluble diastereomeric salt, the improvement comprising adding to said reaction mixture formed in step (ii) an organic or inorganic salt soluble in the liquid phase of said reaction mixture.

10. The process according to claim 9 wherein from about 0.1 to about 10.0 moles of organic or inorganic salt is added to the salt solution based on the moles of organic or inorganic base.

11. The process according to claim 10 wherein about 0.5 to about 5.0 moles of organic or inorganic salt is added.

12. The process according to claim 11 wherein an equimolar amount of said salt is added.

13. The process according to claim 9 wherein said organic salt is an alkali metal, alkaline earth metal or ammonium acetate salt.

14. The process according to claim 13 wherein said salt is a sodium, potassium or ammonium salt.

15. The process according to claim 9 wherein said inorganic salt is an alkali metal, alkaline earth metal or ammonium salt.

16. The process according to claim 15 wherein said salt is a sodium, potassium or ammonium salt.

* * * * *